(12) United States Patent
Dan-Jumbo et al.

(10) Patent No.: US 8,616,050 B1
(45) Date of Patent: Dec. 31, 2013

(54) BOND SURFACE TESTING APPARATUS AND METHOD

(75) Inventors: Eugene Dan-Jumbo, Bothell, WA (US); Joel P. Baldwin, Seattle, WA (US)

(73) Assignee: The Boeing Company, Chicago, IL (US)

(*) Notice: Subject to any disclaimer, the term of this patent is extended or adjusted under 35 U.S.C. 154(b) by 442 days.

(21) Appl. No.: 13/023,682

(22) Filed: Feb. 9, 2011

(51) Int. Cl.
*G01N 19/04* (2006.01)

(52) U.S. Cl.
USPC ........................................... 73/150 A

(58) Field of Classification Search
None
See application file for complete search history.

(56) References Cited

U.S. PATENT DOCUMENTS

| | | | | |
|---|---|---|---|---|
| 3,994,692 | A * | 11/1976 | Rudy | 75/252 |
| 4,797,259 | A * | 1/1989 | Matkovich et al. | 422/534 |
| 7,666,355 | B2 * | 2/2010 | Alavie et al. | 422/65 |

OTHER PUBLICATIONS

"Certification Testing Methodology for Composite Structures, vols. I and II" DOT/FAA/CT-86/39, Oct. 1986.
"Handbook: Manufacturing Advanced Composite Components for Airframes" DOT/FAA/AR-96/75, Apr. 1997.
"Advanced Certification Methodology for Composite Structures" DOT/FAA/AR-96/111, Apr. 1997.
"Effects of Surface Preparation on the Long-Term Durability of Adhesively Bonded Composite Joints" DOT/FAA/AR-03/53, Jul. 2003.
"Bonded Repair of Aircraft Composite Sandwich Structures," DOT/FAA/AR-03/74, Feb. 2004.
"Assessment of Industry Practices for Aircraft Bonded Joints and Structures," DOT/FAA/AR-05/13, Jul. 2005.
"Design of Durable, Repairable, and Maintainable Aircraft Composites," (SAE AE-27, 1997).
"The measurement of surface energy of polymer means of contact angles of liquid on solid structures, A short overview of frequently used methods by Finn Knut Hanson, Department of Chemistry, University of Oslo".
Laser Surface Preparation and Bonding of Aerospace Structural Composites M.A. Belcher, C.J. Wohl, J.W. Connell National Institute of Aerospace, 100 Exploration Way, Hampton, VA 23666, USA NASA Langley Research Center, MS 226, Hampton, VA 23681, USA Corresponding author: M.A. Belcher, tony.belcher@nasa.gov, 1-757-864-1083.
Baldwin et al., "Determining Bond Surface Condition in Composite Structures," U.S. Appl. No. 12/822,610, 38 pages.
Belcher et al., "Laser Surface Preparation and Bonding of Aerospace Structural Composites," 55th International SAMPE Symposium and Exhibition, May 2010, 7 pages.
Hansen, "The Measurement of Surface Energy of Polymer by Means of Contact Angles of Liquids on Solid Surfaces," University of Oslo, 2004, 12 pages.
Woodward, "Prediction of Adhesion and Wetting from Lewis Acid Base Measurements," First Ten Angstroms, Inc., 2000, 6 pages.
Whitehead et al., "Certification Testing Methodology for Composite Structure, vol. I—Data Analysis," Final Report DOT/FAA/CT-86139, Oct. 1986, 100 pages.

(Continued)

*Primary Examiner* — Peter Macchiarolo
*Assistant Examiner* — Alex Devito
(74) *Attorney, Agent, or Firm* — Yee & Associates, P.C.

(57) ABSTRACT

A bond surface testing apparatus includes a solution chamber; a plurality of solutions in the solution chamber, the solution chamber adapted to dispense the solutions onto a bonding surface; an information capture module carried by the solution chamber and adapted to capture information relating to bonding surface properties of the bonding surface; at least one analysis module interfacing with the information capture module and adapted to analyze the bonding surface properties of the bonding surface; and a structural wettability factor prediction module interfacing with the at least one analysis module and adapted to predict a structural wettability factor based on the bonding surface properties.

20 Claims, 4 Drawing Sheets

(56) References Cited

OTHER PUBLICATIONS

Whitehead et al., "Certification Testing Methodology for Composite Structure, vol. II—Methodology Development," Final Report DOT/FAA/CT-86/39, Oct. 1986, 293 pages.

U.S. Department of Transportation Federal Aviation Administraton, "Advanced Certification Methodology for Composite Structures," Final Report DOT/FAA/AR-96/111, Apr. 1997, 167 pages.

U.S. Department of Transportation Federal Aviation Administraton, "Assessment of Industry Practices for Aircraft Bonded Joints and Structures," Final Report DOT/FAA/AR-05/13, Jul. 2005, 245 pages.

U.S. Department of Transportation Federal Aviation Administraton, "Bonded Repair of Aircraft Composite Sandwich Structures," Final Report DOT/FAA/AR-03/74, Feb. 2004, 121 pages.

U.S. Department of Transportation Federal Aviation Administraton, "Effects of Surface Preparation on the Long-Term Durability of Adhesively Bonded Composite Joints," Final Report DOT/FAA/AR-03/53, Jan. 20004, 91 pages.

U.S. Department of Transportation Federal Aviation Administraton, "Handbook: Manufacturing Advanced Composite Components for Airframes," Final Report DOT/FAA/AR-96/75, Apr. 1997, 226 pages.

USPTO Office Action, dated May 14, 2012, regarding U.S. Appl. No. 12/822,610, 10 pages.

Notice of Allowance, dated Oct. 29, 2012, U.S. Appl. No. 12/822,610, 13 pages.

Supplemental Notice of Allowance, dated Nov. 6, 2012, regarding U.S. Appl. No. 12/822,610, 5 pages.

\* cited by examiner

BOND SURFACE TESTING APPARATUS AND METHOD

TECHNICAL FIELD

The disclosure generally relates to apparatuses and methods for testing bonding suitability of structural composite bonding surfaces. More particularly, the disclosure generally relates to a bond surface testing apparatus and method capable of measuring characteristics of a bonding surface via surface energies that are activated on the bonding surface and then converted into a series of complex mathematical algorithms which output a calculated quality bonding factor that is based on the three-dimensional wettability surface energies of the bonding surface and indicates whether the bonding surface is suitable for bonding.

BACKGROUND

Currently, prepared structural composite bonding surfaces which are intended for structural bonding with another material are not certifiable prior to bonding. Thus, much expense may be wasted in scraps due to the poor bonding quality of bonding surfaces on composites. Conventional design and maintenance practices may not solely rely on the performance of a bonded joint or repair on composites for structural certification. As bonded composite structures become more common as a way to reduce weight and improve airframe performance in modern aircraft, reliable methods may be required to directly certify the quality of the bonded joints between composites without adding additional contaminants that may negate their structural benefits. In addition, the use of structural bonding repair techniques, compared to mechanically-fastened joints, may become more viable as a long-term repair solution. Like composite bonded structures, bonded repairs may require a certification method to ensure the structural quality of the bonding surfaces which form the bond between composites.

One current solution for ensuring that an optimum structural bond surface exists on a composite structure may rely on tight process controls and skill of technicians to ensure quality and consistency. In some cases, cleanliness and roughness of the bonding surface may be measured and compared to an acceptable range to provide an inline process check. However, none of the known available methods can quantify and certify the bonding surface itself prior to structural bonding. Such a certification method would create confidence in the long-term durability of the bonded joint between composites after the structure which includes the bonded joint enters service. Individual surface characterization techniques that provide information on a single surface variable, such as surface roughness or active contaminants via profilometry or X-ray photoelectron spectroscopy (XPS), respectively, exist. However, both profilometry and XPS typical data may not quantify the structural bonding surface in terms of readiness to meet long-term structural joint durability, static strength and damage tolerance capability.

Conventional methods may not provide quantifiable engineering data related to the just-prepared structural bonding barrel surface quality or its bond durability. Moreover, such methods may not be compatible for localized use on the composite structures which are being bonded. Additionally, the existing techniques may not account for the potentially wide variations of the measured results on the structural bonding surface. Even a minimum of engineering data, such as surface roughness, for example, can vary greatly when the bonding surface is prepared per procedure via hand sanding methods, grit blasting and laser techniques.

Therefore, a bond surface testing apparatus and method are needed which are capable of measuring characteristics of a bonding surface via surface energies that are activated on the bonding surface and then converted into a series of complex mathematical algorithms which output a calculated quality bonding factor that is based on the three-dimensional wettability surface energies of the bonding surface and indicates whether the bonding surface is suitable for bonding.

SUMMARY

The disclosure is generally directed to a bond surface testing apparatus for testing bonding suitability of a bonding surface. An illustrative embodiment of the apparatus includes a solution chamber; a plurality of solutions in the solution chamber, the solution chamber adapted to dispense the solutions onto the bonding surface; an information capture module carried by the solution chamber and adapted to capture information relating to bonding surface properties of the bonding surface; at least one analysis module interfacing with the information capture module and adapted to analyze the bonding surface properties of the bonding surface; and a structural wettability factor prediction module interfacing with the at least one analysis module and adapted to predict a structural wettability factor based on the bonding surface properties.

In some embodiments, the bond surface testing apparatus may include a solution chamber; a plurality of solutions in the solution chamber, the solution chamber adapted to dispense the solutions onto the bonding surface; a pair of stand-offs adapted to engage the bonding surface; an information capture module carried by the stand-offs and adapted to capture information relating to bonding surface properties of the bonding surface; a data transfer pathway interfacing with the information capture module; a plurality of analysis modules interfacing with the data transfer pathway and adapted to analyze the bonding surface properties of the bonding surface; and a structural wettability factor prediction module interfacing with the data transfer pathway and adapted to predict a structural wettability factor based on the bonding surface properties.

The disclosure is further generally directed to a bond surface testing method. An illustrative embodiment of the method includes providing a plurality of solutions; activating functional groups on a bonding surface by dispensing the plurality of solutions onto the bonding surface; analyzing bonding surface properties on the bonding surface; and predicting a structural wettability factor based on the bonding surface properties.

BRIEF DESCRIPTION OF THE ILLUSTRATIONS

DETAILED DESCRIPTION

Figure 1:
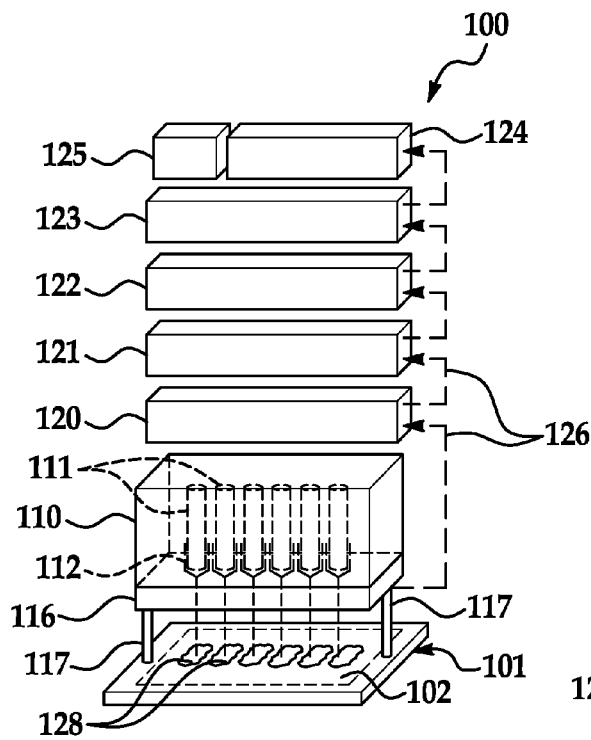
FIG. 1 is an exploded perspective view of an illustrative embodiment of the bond surface testing apparatus.

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the embodiments of the disclosure which are defined by the claims. Furthermore, there is no intention to be bound by any expressed or implied theory presented in the preceding technical field, background, brief summary or the following detailed description.

The disclosure is generally directed to a bond surface testing apparatus which may activate surface energies of functional groups on a bonding surface and then analyze various chemical and mechanical bonding surface properties using a series of complex mathematical algorithms. The functional groups which are activated may be those which are involved in bonding of the bonding surface with a second bonding surface. The apparatus may match the analyzed bonding surface properties of the bonding surface with three-dimensional wettability curves to determine convergence of the bonding surface properties with the three-dimensional wettability curves. Based on the convergence of the measured and analyzed bonding surface properties with the three-dimensional wettability curves, the apparatus may output a calculated quality bonding factor. The outputted quality bonding factor may indicate the bonding suitability of the bonding surface. Accordingly, the quality bonding factor may indicate whether the tested bonding surface on the structure is ready for production bonding or repair bonding with another structure or alternatively, whether the bonding surface requires preparation prior to bonding. In some applications, the quality bonding factor may be used to certify the bonding suitability of a bonding surface.

In some embodiments, the apparatus may be a portable handheld apparatus. The apparatus may be compact in design and utilized on a factory or shop floor for quick turnaround of both measurements of bonding engineering data and decisions related to the bonding suitability of a prepared structural composite surface for the operational life of the structure.

The apparatus may include integrated device components and process steps which may include multiple known solutions; a complex solution chamber with multiple solution containers containing the known solutions and capable of dispensing the known solutions in predetermined volumes onto a bonding surface of a structure to activate surface energies of functional groups on the bonding surface; and various analysis modules for analyzing bonding surface properties of the bonding surface. In some embodiments, the analysis modules of the apparatus may include a functional group analysis module for analyzing the functional groups on the bonding surface; a surface energy analysis module for analyzing the surface energies of the functional groups on the bonding surface; and a chemical-mechanical analysis module for computing the micro-chemical mechanics forces present on the bonding surface. The apparatus may further include a structural wettability factor (quality bonding factor) prediction module for prediction of the convergence of the three-dimensional wettability curves with the bonding surface properties which are based on the functional group analysis, the surface energy analysis and the chemical-mechanical characteristic analysis of the bonding surface; and a structural wettability factor printer for printing go/no-go quality bonding factor phi (Ø) which indicates bonding suitability based on the convergence of the three-dimensional wettability curves with the bonding surface properties.

Figure 2:
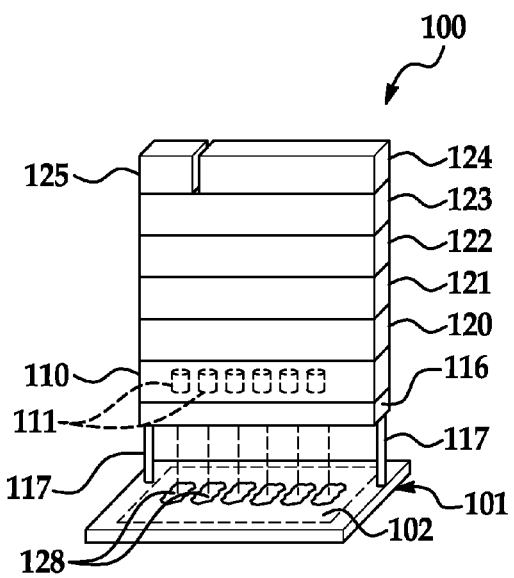
FIG. 2 is a perspective view of an illustrative embodiment of the bond surface testing apparatus in exemplary application of the apparatus.

Referring to FIGS. 1 and 2, an illustrative embodiment of the bond surface testing apparatus, hereinafter apparatus, is generally indicated by reference numeral 100. The apparatus 100 may be used to determine the bonding suitability of a bonding surface (not shown) on a structural composite bonding element (not shown). In some applications, the structural composite bonding element may be a component of an aircraft fuselage, for example and without limitation. The apparatus 100 may be applicable to certification of the bonding surface of a structural composite bonding element in order to ensure the quality of structural bonds in which the structural composite bonding element is bonded to another bonding surface in production or repair of a structure.

As will be hereinafter further described, the apparatus 100 may be adapted to contain and dispense solutions 128 having known chemical characteristics or properties onto a bonding surface 102 of a composite structure 101. The solutions 128 dispensed onto the bonding surface 102 of the composite structure 101 may activate surface energies of functional groups on the bonding surface 102. The functional groups which are activated on the bonding surface 102 may be the functional groups which would be involved in bonding of the bonding surface 102 to another bonding surface. The activated surface energies of the functional groups on the bonding surface 102 may substantially mimic the surface energies of the functional groups on the bonding surface the bonding suitability of which is to be tested. Using mathematical algorithms, the apparatus 100 may be adapted to analyze bonding surface properties which may include analysis of the functional groups, the surface energies of the functional groups which are activated on the bonding surface 102 by the known solutions 128 and the micro-chemical mechanics forces present on the bonding surface 102. The apparatus 100 may be adapted to predict convergence of three-dimensional wettability tension surface energy curves based on the analyzed bonding surface properties of the bonding surface 102 by matching the three-dimensional wettability curves to the bonding properties. The apparatus 100 may additionally be adapted to formulate a bonding quality factor phi (Ø) which indicates bonding suitability based on the convergence of the three-dimensional wettability curves with the bonding properties. In some embodiments, the apparatus 100 may be adapted to print the bonding quality factor (Ø).

The apparatus 100 may include a solution chamber 110. Multiple solution containers 111 may be provided in the solution chamber 110. The solution containers 111 may be arranged in adjacent relationship with respect to each other in the solution chamber 110. Each of the solution containers 111 may be adapted to contain a known solution 128 which will be used to activate surface energies of chemical functional groups on a bonding surface 102 of a composite structure 101. Bonding surface properties which may include surface energies of the functional groups and the micro-chemical mechanics forces present on the bonding surface 102 may be analyzed and matched with three-dimensional wettability curves using mathematical algorithms. The apparatus 100 may be adapted to predict the convergence of the three-dimensional wettability curves with the bonding surface properties. Based on the convergence of the three-dimensional wettability curves with the bonding surface properties, the apparatus 100 may be adapted to predict the bonding suitability a bonding surface on a structural composite bonding element (not shown) which is represented by the bonding surface 102 of the composite structure 101.

In some applications, the composite structure 101 may be a traveler element having the bonding surface 102 which mimics the bonding properties of the functional groups on the bonding surface being tested. Each solution container 111 may include a microfluidic pipette and activator 112 which is adapted to dispense a selected volume of the solution 128 from the solution container 111 onto the bonding surface 102. Accordingly, the solutions 128 can be selectively dispensed from the solution containers 111 onto the bonding surface 102 to activate the known surface energies of the functional groups and create the micro-chemical mechanics forces present on the bonding surface 102 in a manner which corresponds to the surface energies and micro-chemical mechanics forces of the functional groups on the bonding surface which is to be tested.

The apparatus 100 may include an information capture module 116. The information capture module 116 may be adapted to capture information which relates to the bonding surface properties of the bonding surface 102. Stand-offs (or support for forming a solution clearance gap) 117 may interface with the information capture module 116. The stand-offs 117 may be adapted to engage the composite structure 101 during operation of the apparatus 100.

A functional group analysis module 120, a surface energy analysis module 121, a chemical-mechanical analysis module 122, a structural wettability factor prediction module 123 and a structural wettability factor printer 124 may interface with the information capture module 116 through a data transfer pathway 126. In some embodiments, a battery 125 may interface with the structural wettability factor printer 124 and other components of the apparatus 100.

A set of the known solutions 128 may be developed for each of the structural composite bonding elements the bonding suitability of which are to be tested using the apparatus 100. The solutions 128 may be developed according to previously-identified surface energies and wettability tension data of the bonding surfaces of the elements prior to bonding. For example and without limitation, structural bismaleimide (BMI) composite surface (primarily the BMI matrix material) have both dispersive, polar and modified luftiz acid-base surface energies on the structural composite bonding element which is to be bonded to another surface. Accordingly, the solutions 128 which are dispensed onto the bonding surface 102 may include structural BMI which imparts the corresponding bonding surface properties (surface energies and micro-chemical mechanics forces) to the functional groups on the bonding surface 102. The apparatus 100 may computationally combine the structural BMI bonding surface properties of the functional groups with the matching wettability tension curves of the structural composite bonding element to formulate a quality bonding factor (Ø). The quality bonding factor (Ø) may indicate whether the prepared bonding surface of the element is ready to be bonded.

In application of the apparatus 100, the bonding surface 102 of the composite structure 101 may be treated with the solutions 128 with known chemistries relative to the surface energies of functional groups on the bonding surface of the structural composite bonding element which is to be tested.

After treatment with the solutions 128, the bonding surface 102 may include both functionalized units and micro-liter volumes of the liquid solutions 128 which are similar to those of the structural composite bonding element which is to be bonded to another element. In some applications of the apparatus 100, the composite structure 101 may be a composite test specimen (or commonly known as a traveler element) which is prepared under identical conditions as the structural composite bonding element which is to be tested. Accordingly, the composite structure 101 may be selectively removed from the apparatus 100 for further analysis after implementation of the apparatus 100.

The functional group analysis module 120, the surface energy analysis module 121, the chemical-mechanical analysis module 122 and the structural wettability factor prediction module 123 of the apparatus 100 may utilize mathematical algorithms to analyze the bonding surface properties of the bonding surface 102 and formulate a structural wettability or bonding quality factor (Ø) which may be used to determine whether the bonding surface 102 is suitable for forming quality bonding with a structural element in production or repair applications. The analysis may be carried out using known principles of polymer chemistry. The functional group analysis module 120 may capture identification of the bonding functional groups which each of the solutions 128 impart to the bonding surface 102.

Surface tension measurements for formulation of the wettability prediction factor (bonding quality factor) on the bonding surface 102 may be analyzed by the functional group analysis module 120 of the apparatus 100 using equations E1, E2a, E2b, E3, E4 and E5. Equation (E1) below accounts for the effect of adsorption of chemical species to the bonding surface 102 on the solid-vapor interface and liquid-vapor interface:

$$\Delta G_1{}^G = -\gamma_{iv}(1+\cos\emptyset) \qquad \text{E1}$$

Equations (E2a) and (E2b) below describe the equilibrium film pressure of a composite structure the contact angle of which is less than zero.

$$\gamma_z - \gamma_{zv} = \Pi_{\emptyset sv} \qquad \text{E2a}$$

$$\gamma_s - \gamma_{sv} = \Pi_{\emptyset iv} \qquad \text{E2b}$$

The testing, $\Pi_{esl}$, may be included in equation (E3) below representing the solid-liquid interface:

$$\gamma_s - \Pi_{\emptyset sw} - \gamma_{si} = (\gamma_l - \Pi_{\emptyset iv})\cos\emptyset \qquad \text{E3}$$

The Wenzel equation (equation E4 below) may be used to describe the combined influence of hysteresis to measure the accurate contact angle where γ is the ratio of the supposed area to the prepared area outer plane and Ø is the contact angle of the liquid on the bonding surface 102.

$$\gamma = \cos\emptyset/\cos\emptyset' \qquad \text{E4}$$

The inclusion of the Fox-Zisman method in analyzing the accuracy of the contact angle Ø is important in that the equation provides a more accurate estimate of $\gamma_s$ of the composite structure to be bonded from the plot of Ø (contact angle) vs. the surface energies. This relationship may approximate a straight line described by equation (5) below:

$$\cos\emptyset = 1 - b(\gamma_l - \gamma_c) \qquad \text{E5}$$

The value $\gamma_c$ of $\gamma_l$ is a facet of parameter to combine with the modified Lifshitz equation to yield a combined surface energy that is a consequence of both electromagnetic interactions and contact angle measurements from the Fox-Zisman equation.

The surface energy analysis module 121 of the apparatus 100 may capture identification of the bonding functional groups of each of the solutions 128 on the bonding surface 102 from the functional group analysis module 120 and compute the surface tensions of the functional groups as was heretofore described. These data may be transmitted to the computational chemical-mechanical analysis module 122, which may compile the data and predict three-dimensional wettability curves for the bonding surface 102. The structural wettability factor prediction module 123 may predict a wettability curve factor by comparing the previously-computed bonding surface properties of the functional groups activated by the solutions 128 to the predicted three-dimensional structural wettability curves computed by the chemical-mechanical analysis module 122. The structural wettability factor prediction module 123 may use the wettability curve factor to determine the bonded repair or bonded structure quality in the form of a bonding quality factor phi (Ø). The structural wettability factor printer 104 may print the bonding quality factor (Ø).

The use of the molecular theory of contact angle in a polar system, which is well-developed in polymer chemistry, can be combined to estimate the surface energy of the composite bonded structure mathematically by cohesive energies of the two phases. Composite structure and the wettability tensions of the adhesive system can be combined with the polar solutions to develop the individual surface energies close to the individual adhesive systems for bonding with the structural composite as shown in the cohesive energy equation in equation (6) below:

$$\Delta G_{ij} = \sqrt{\Delta} G_i^0 - \Delta G_j^0 = -2\sqrt{\gamma_i \gamma_j} - \Delta G_{ij}^a / \sqrt{\Delta G_i^c \Delta G_i^c} = 1 \quad E6$$

where i and j are both polar.

Equation (6) may then be used to predict the composite structural surface energy and the adhesive wettability tensions to form predicted three-dimensional curves for the particular composite structures type. The resultant computed experimental exponent is provided as equation (7) and equation (8):

$$\emptyset(\exp) = \gamma_i + \gamma_j - \gamma_{ij}/2\sqrt{\gamma_i \gamma_j} \quad E7$$

$$\Delta G_{ij}^a / \sqrt{(\Delta G_i^0 \Delta G_j^0)} = \emptyset \quad E8$$

These thermodynamic cohesion processes and thermodynamic adhesion processes represent the idealization of free surface energy models employing thermodynamic terms of $\Delta G = 2\gamma - w^C$.

where $\Delta G^C = -2\gamma = -w^c$; and, where $\Delta G_{ij} = \gamma_{ij} - \gamma_i - \gamma_j = -w_{ij}^c$ This emphasizes the fact that γ is indeed a physical entity in terms of free energy per area or force per unit length as shown in the two diagrams, respectively. This is represented in the cohesion and adhesion pressure, which is the interaction between the different solid/liquid interfaces and others.

Figure 4:
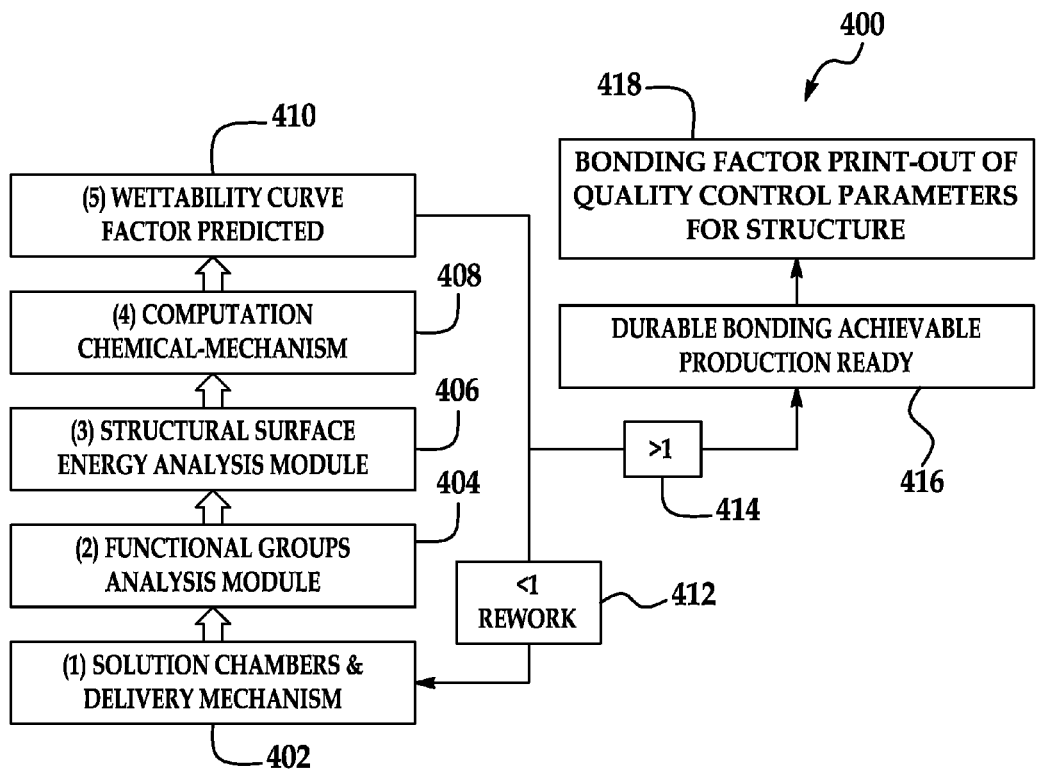
FIG. 4 is a flow diagram of an illustrative embodiment of the bond surface testing method.

Referring to FIG. 4, a flow diagram 400 which illustrates an illustrative embodiment of the bond surface testing method is shown. The method may be carried out in implementation of the apparatus 100 which was heretofore described with respect to FIGS. 1 and 2. In block 402, the solution chamber 110 of the apparatus 100 dispenses known solutions 128 onto a bonding surface 102 of a composite structure 101. In block 404, the functional group analysis module 120 of the apparatus 100 may identify functional groups which the solutions 128 activate on the bonding surface 102. In block 406, the structural surface energy analysis module 121 of the apparatus 100 may analyze surface tensions and pressures on the bonding surface 102. In block 408, the chemical-mechanical analysis module 122 of the apparatus 100 may predict three-dimensional wettability curves based on the bonding surface property data obtained from the functional group analysis module 120 and the surface energy analysis module 121. In block 410, the structural wettability factor prediction module 123 of the apparatus 100 may predict a bonding quality factor by matching the surface energies of the functional groups on the bonding surface with the three-dimensional wettability curves.

In the event that the bonding quality factor predicted in block 410 is less than one, the method may return to block 402. In the event that the bonding quality factor predicted in block 410 is greater than one (block 414), durable bonding is achievable and production is ready in block 416. In block 418, the structural wettability factor printer 124 of the apparatus 100 may print out quality control parameters for the structure to be bonded.

Figure 3:
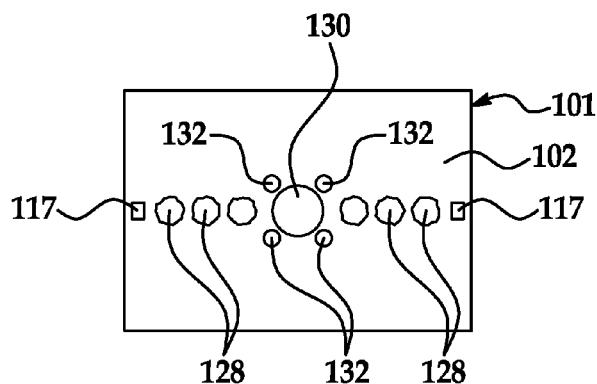
FIG. 3 is a top view of a composite structure tested for bonding production quality readiness in exemplary application of the apparatus.
Figure 5A:
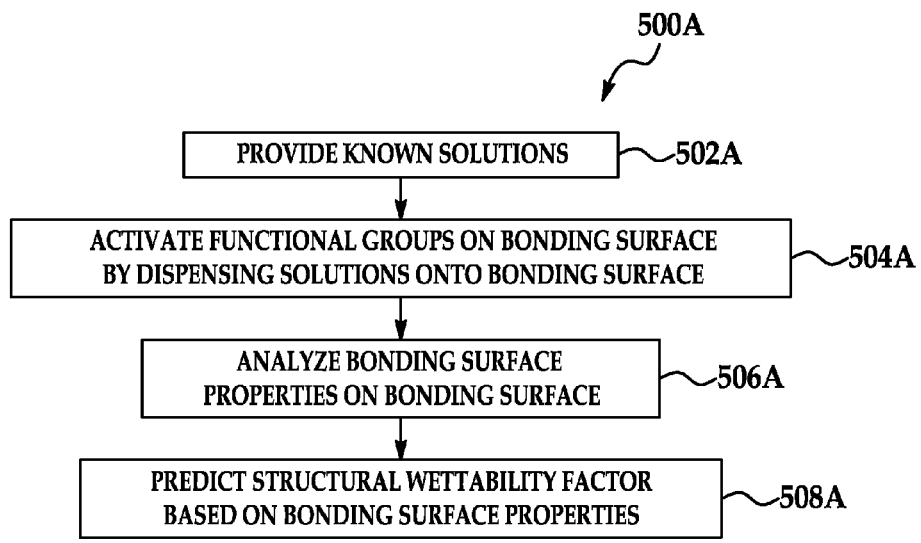
FIG. 5A is a flow diagram which summarizes an illustrative embodiment of a bond surface testing method.
Figure 5:
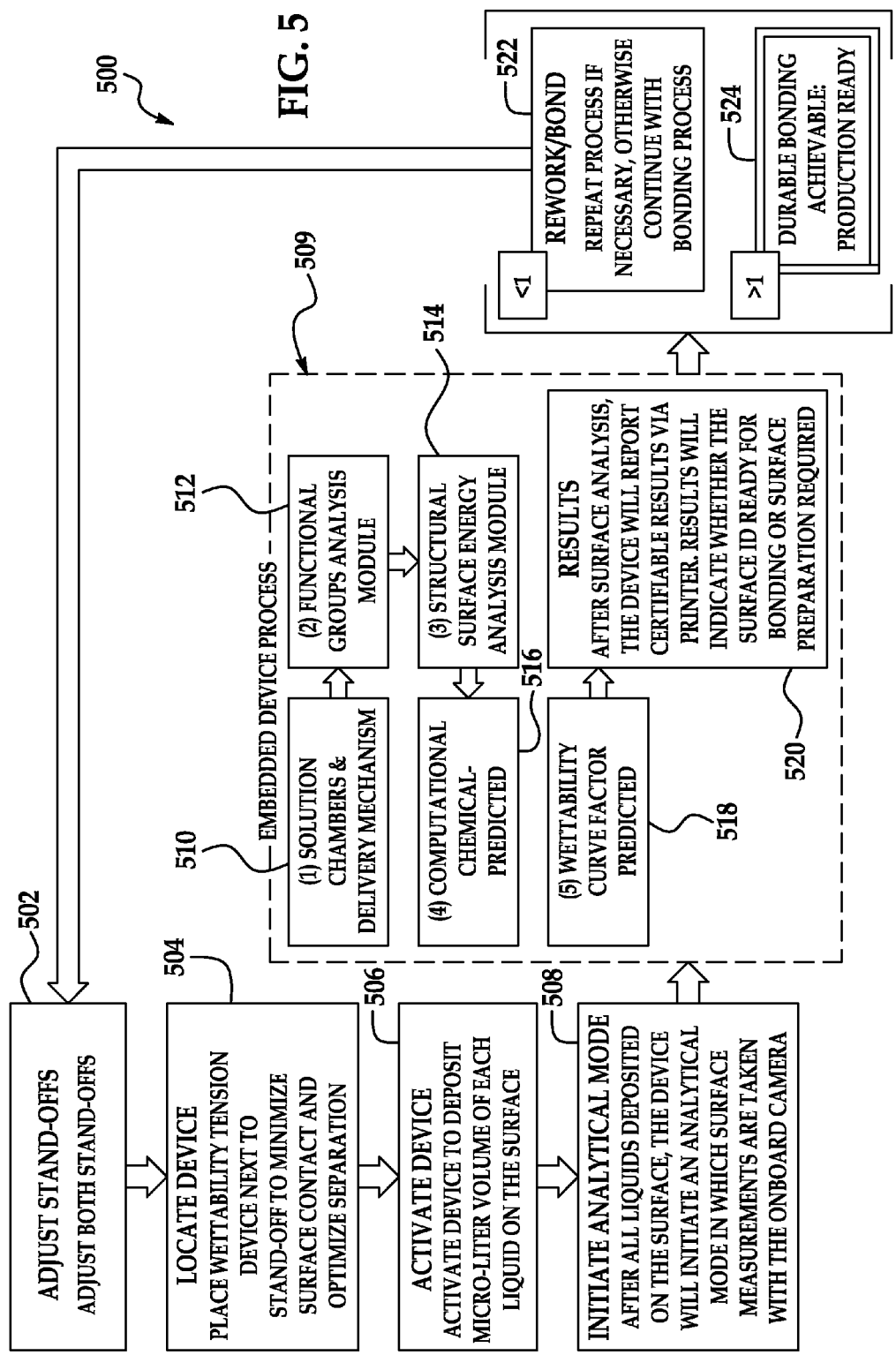
FIG. 5 is a functional block diagram which illustrates operation of an illustrative embodiment of the bond surface testing apparatus in exemplary application of the apparatus.

Referring next to FIGS. 1-3 and 5, a functional block diagram 500 which illustrates exemplary operation of an illustrative embodiment of the bond surface testing apparatus 100 is shown in FIG. 5. In block 502, the stand-offs 117 (FIGS. 1 and 2) of the apparatus 100 may be adjusted on the bonding surface 102 of the composite structure 101. In some applications, the stand-offs 17 may be a distance allowing the solution to clear the surface tension. In block 504, the apparatus 100 may be located on the bonding surface 102. The stand-offs 117 may be adjusted to minimize surface contact and optimize separation on the bonding surface 102. In block 506, the apparatus 100 may be activated. Accordingly, a micro-liter volume of each solution 128 may be deposited from each solution container 111 of the solution chamber 110 onto the bonding surface 102. In block 508, after all solutions 128 have been deposited onto the bonding surface 102, the apparatus 100 may initiate an analytical mode 509 in which surface measurement images 130 (FIG. 3) are taken with an onboard camera (not shown). As shown in FIG. 3, in some applications, onboard LEDs 132 may illuminate the bonding surface 102.

As shown in FIG. 5, in some embodiments, the analytical mode 509 may include operation of the solution chamber 110 to deposit the solutions 128 onto the bonding surface 102 (block 510); functional group identification by the functional group analysis module 120 (block 512); structural surface energy analysis by the structural surface energy analysis module 121 (block 514); computation of three-dimensional wettability curves by the chemical-mechanical analysis module 122 (block 516) based on the functional group analysis and the structural surface energy analysis; prediction of a wettability curve or bonding quality factor by the structural wettability factor prediction module 123 (block 518); and printing of the structural wettability factor with certifiable results by the structural wettability factor printer 124 (block 520). The certifiable results may indicate whether the surface is ready for bonding or surface preparation is required prior to bonding.

If the structural wettability factor predicted in block 518 and printed in block 520 is less than one, the method may return (block 522) to block 502 and blocks 504-520 may be repeated. If the structural wettability factor is greater than one, the method may proceed to block 524 in which durable bonding is achievable and bonding production can proceed.

Referring next to FIG. 5A, a flow diagram 500A which summarizes an illustrative embodiment of the bond surface testing method is shown. In block 502A, known solutions are provided. In block 504A, functional groups on a bonding surface are activated by dispensing the solutions onto the bonding surface. In block 506A, bonding surface properties on the bonding surface are analyzed. In some embodiments, analyzing bonding surface properties may include identifying functional groups on the bonding surface. In some embodiments, analyzing bonding surface properties may include analyzing surface energies on the bonding surface. In some embodiments, analyzing bonding surface properties may include predicting three-dimensional wettability curves based on the bonding surface properties. In block 508A, a structural wettability factor is predicted based on the bonding surface properties. In some embodiments, predicting a structural wettability factor based on the bonding surface properties comprises may include predicting a structural wettability factor by matching the three-dimensional wettability curves with the surface energies on the bonding surface.

Figure 6:
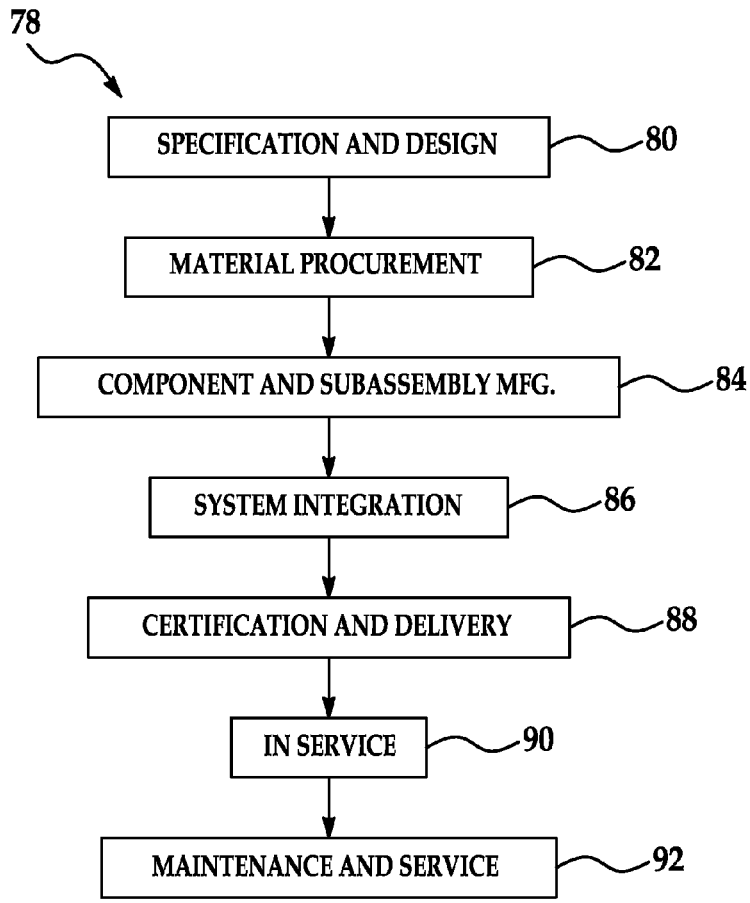
FIG. 6 is a flow diagram of an aircraft production and service methodology.
Figure 7:
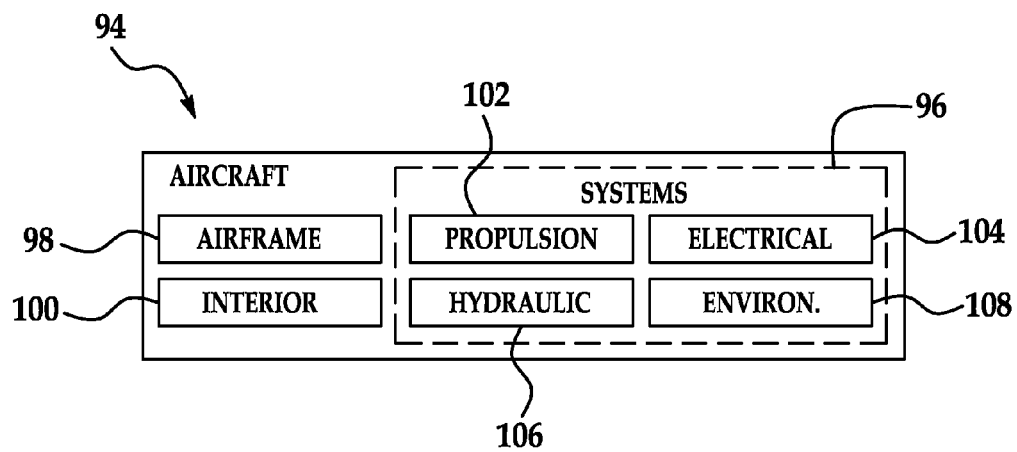
FIG. 7 is a block diagram of an aircraft.

Referring next to FIGS. 6 and 7, embodiments of the disclosure may be used in the context of an aircraft manufacturing and service method 78 as shown in FIG. 6 and an aircraft 94 as shown in FIG. 7. During pre-production, exemplary method 78 may include specification and design 80 of the aircraft 94 and material procurement 82. During production, component and subassembly manufacturing 84 and system integration 86 of the aircraft 94 takes place. Thereafter, the aircraft 94 may go through certification and delivery 88 in order to be placed in service 90. While in service by a customer, the aircraft 94 may be scheduled for routine maintenance and service 92 (which may also include modification, reconfiguration, refurbishment, and so on).

Each of the processes of method 78 may be performed or carried out by a system integrator, a third party, and/or an operator (e.g., a customer). For the purposes of this description, a system integrator may include without limitation any number of aircraft manufacturers and major-system subcontractors; a third party may include without limitation any number of vendors, subcontractors, and suppliers; and an operator may be an airline, leasing company, military entity, service organization, and so on.

As shown in FIG. 7, the aircraft 94 produced by exemplary method 78 may include an airframe 98 with a plurality of systems 96 and an interior 100. Examples of high-level systems 96 include one or more of a propulsion system 102, an electrical system 104, a hydraulic system 106, and an environmental system 108. Any number of other systems may be included. Although an aerospace example is shown, the principles of the invention may be applied to other industries, such as the automotive industry.

The apparatus embodied herein may be employed during any one or more of the stages of the production and service method 78. For example, components or subassemblies corresponding to production process 84 may be fabricated or manufactured in a manner similar to components or subassemblies produced while the aircraft 94 is in service. Also one or more apparatus embodiments may be utilized during the production stages 84 and 86, for example, by substantially expediting assembly of or reducing the cost of an aircraft 94. Similarly, one or more apparatus embodiments may be utilized while the aircraft 94 is in service, for example and without limitation, to maintenance and service 92.

Although the embodiments of this disclosure have been described with respect to certain exemplary embodiments, it is to be understood that the specific embodiments are for purposes of illustration and not limitation, as other variations will occur to those of skill in the art.

What is claimed is:

1. A bond surface testing apparatus for testing bonding suitability of a bonding surface, comprising:
    a solution chamber;
    a plurality of solutions in said solution chamber, said solution chamber adapted to dispense said solutions onto the bonding surface;
    an information capture module carried by said solution chamber and adapted to capture information relating to bonding surface properties of the bonding surface;
    at least one analysis module interfacing with said information capture module and adapted to analyze said bonding surface properties of the bonding surface; and
    a structural wettability factor prediction module interfacing with said at least one analysis module and adapted to predict a structural wettability factor based on said bonding surface properties.

2. The apparatus of claim 1 further comprising a structural wettability factor printer interfacing with said structural wettability factor prediction module and adapted to print said structural wettability factor.

3. The apparatus of claim 1 further comprising a plurality of solution containers in said solution chamber and wherein said plurality of solutions are contained in said plurality of solution containers, respectively.

4. The apparatus of claim 3 further comprising a plurality of microfluidic pipettes and actuators interfacing with said plurality of solution containers, respectively, and adapted to dispense said solutions onto the bonding surface.

5. The apparatus of claim 1 wherein said at least one analysis module comprises a functional group analysis module adapted to identify functional groups on the bonding surface.

6. The apparatus of claim 5 wherein said at least one analysis module comprises a surface energy analysis module adapted to analyze surface energies of said functional groups on the bonding surface.

7. The apparatus of claim 6 wherein said at least one analysis module comprises a chemical-mechanical analysis module adapted to predict three-dimensional wettability curves based on data from said functional group analysis module and said surface energy analysis module.

8. The apparatus of claim 7 wherein said structural wettability factor prediction module is adapted to predict said structural wettability factor by matching said three-dimensional wettability curves with said surface energies of said functional groups on the bonding surface.

9. A bond surface testing apparatus for testing bonding suitability of a bonding surface, comprising:
    a solution chamber;
    a plurality of solutions in said solution chamber, said solution chamber adapted to dispense said solutions onto the bonding surface;
    a pair of stand-offs adapted to engage the bonding surface;
    an information capture module carried by said stand-offs and adapted to capture information relating to bonding surface properties of the bonding surface;
    a data transfer pathway interfacing with said information capture module;
    a plurality of analysis modules interfacing with said data transfer pathway and adapted to analyze said bonding surface properties of the bonding surface; and
    a structural wettability factor prediction module interfacing with said data transfer pathway and adapted to predict a structural wettability factor based on said bonding surface properties.

10. The apparatus of claim 9 further comprising a structural wettability factor printer interfacing with said data transfer pathway and adapted to print said structural wettability factor.

11. The apparatus of claim 9 further comprising a plurality of solution containers in said solution chamber and wherein said plurality of solutions are contained in said plurality of solution containers, respectively.

12. The apparatus of claim 11 further comprising a plurality of microfluidic pipettes and actuators interfacing with said plurality of solution containers, respectively, and adapted to dispense said solutions onto the bonding surface.

13. The apparatus of claim 9 wherein said plurality of analysis modules comprises a functional group analysis module adapted to identify functional groups on the bonding surface.

14. The apparatus of claim 13 wherein plurality of analysis modules comprises a surface energy analysis module adapted to analyze surface energies of said functional groups on the bonding surface.

15. The apparatus of claim 14 wherein said plurality of analysis modules comprises a chemical-mechanical analysis module adapted to predict three-dimensional wettability curves based on data from said functional group analysis module and said surface energy analysis module.

16. The apparatus of claim 15 wherein said structural wettability factor prediction module is adapted to predict said structural wettability factor by matching said three-dimensional wettability curves with said surface energies of said functional groups on the bonding surface.

17. A bond surface testing method, comprising:
providing a plurality of solutions;
activating functional groups on a bonding surface by dispensing said plurality of solutions onto said bonding surface;
analyzing bonding surface properties on said bonding surface; and
predicting a structural wettability factor based on said bonding surface properties.

18. The method of claim 17 wherein said analyzing bonding surface properties comprises identifying functional groups on said bonding surface.

19. The method of claim 18 wherein said analyzing bonding surface properties comprises analyzing surface energies on said bonding surface.

20. The method of claim 19 wherein said analyzing bonding surface properties comprises predicting three-dimensional wettability curves based on said bonding surface properties.

\* \* \* \* \*